United States Patent [19]
Hovis et al.

[11] Patent Number: 5,729,341
[45] Date of Patent: Mar. 17, 1998

[54] METHOD AND APPARATUS FOR TESTING MATERIALS FOR USE IN A LASER RESONATOR

[75] Inventors: Floyd E. Hovis, Apopka; Bart A. Shepherd, Winter Park; Chris Radcliffe, Orlando; Steve Guch, Jr., Longwood, all of Fla.

[73] Assignee: Litton Systems, Inc., Woodland Hills, Calif.

[21] Appl. No.: 614,528

[22] Filed: Mar. 13, 1996

[51] Int. Cl.⁶ .......................... G01N 21/01; G01N 21/00
[52] U.S. Cl. .......................... 356/244; 356/256; 356/239
[58] Field of Search .......................... 356/239, 240, 356/244, 256; 73/866; 372/92, 98, 99

[56] References Cited

U.S. PATENT DOCUMENTS

| | | | |
|---|---|---|---|
| 3,794,431 | 2/1974 | Rothrock | 356/256 |
| 3,999,865 | 12/1976 | Milam et al. | 356/239 |
| 5,417,494 | 5/1995 | Kempa et al. | 374/5 |
| 5,440,143 | 8/1995 | Carangelo et al. | 250/573 |

*Primary Examiner*—Frank G. Font
*Assistant Examiner*—Amanda Merlino
*Attorney, Agent, or Firm*—William M. Hobby, III

[57] ABSTRACT

A method and apparatus for testing materials for use in a laser resonator includes selecting a test fixture apparatus having a housing with an internal chamber volume selected to approximate the internal volume of a predetermined laser resonator and having a pair of sealed windows therein which are removably attached to the housing and having optical coatings selected to match the coating on the optics of a laser. The housing has a removable cover and a gas purging opening. A laser of a predetermined wavelength and power is mounted adjacent the test fixture and is aligned for directing the laser beam through both of the windows of the test fixture. A material is placed in the test fixture and a laser beam directed through the coated windows for a predetermined period of time and thereafter the coated windows are examined for damage or contamination. The test fixtures are also cleaned and certified prior to testing so that a preselected test fixture can determine damage for selective materials used therein.

14 Claims, 1 Drawing Sheet

METHOD AND APPARATUS FOR TESTING MATERIALS FOR USE IN A LASER RESONATOR

BACKGROUND OF THE INVENTION

The present invention relates to an apparatus and method for testing materials for use in a resonator and especially to a method and apparatus which test materials for potential damage or contamination to laser optics.

It has been observed in the past that sealed laser resonators frequently experience long term optical damage which limits the useful life of the laser. Testing by Applicant has shown that much of the damage is due to the presence of contaminants that had out-gassed from materials or assemblies used to build the laser or that were introduced by processes used to build the laser. Prior practice relied on measures of the total mass loss and collected volatile condensible material to determine whether a material was suitable for use in the presence of the sensitive optics used in a resonator. In this connection, a set of tables for the total mass loss (TML) and for the collected volatile condensible material (CVCM) has been developed by NASA for material verification. A typical requirement on a material for use in a sealed compartment with sensitive optics is that it have a total mass loss (TML) of less than 1% and a CVCM of less than 0.1%. However, Applicants have been able to show that a number of materials which meet the TML and CVCM specifications will still induce optical damage in a laser resonator. In the past, assembly screening was accomplished on the building assembles of materials that passed the TML and CVCM criteria. Screening for processes relied mainly on techniques for the detection of residual contaminants left by the processes with limited knowledge of the amount of the contaminants required to cause laser induced optical damage. This can lead to extensive work to reduce the level of contaminant.

The present invention allows the quantification of the amount of various contaminants that will cause laser induced optical damage without damaging the laser or laser optics.

In the prior art, a method and apparatus for standardizing optical pumped laser materials have been known in the past, as shown in the Rothrock U.S. Pat. No. 3,794,431, for a Method and Apparatus for Standardizing Optically Pumped Laser Materials. This system includes a given light pumping lamp of defined energy output along with a given access area and a fixed light for receiving laser materials and a resonant or optical cavity for the access area of given defined characteristics. The arrangement is such that any reflected radiation from a lamp is prohibited from passing into the access area. Successive laser materials are received in the access area and subjected to substantially identical light pumping conditions to cause stimulated emission of laser light and the output laser light of each material monitored so that the materials can be characterized in accordance with their output characteristics. The Carangelo et al. U.S. Pat. No. 5,440,143, teaches a Folded-Path Optical Analysis Gas Cell which employs an elliptical concave mirror and two substantially spherical concave mirrors. This patent accomplishes path lengthening in a folded path cell for measuring optical absorption of gas samples. In the Kempa et al. U.S. Pat. No. 5,417,494, a Contactless Testing of Electronic Materials and Devices Using Microwaves is provided in which a volume of material is placed in a closed container having an opening for directly microwave radiation into the sealed chamber of a preselected wavelength. The chamber also has an inlet for an infrared camera.

In contrast to the prior art, the present invention allows a means for screening for selection of materials, assembly and processes that do not cause contamination induced damage and thus extend the useful lifetime of a sealed laser resonator. The invention allows the screening of complete assemblies for their potential to cause laser induced optical damage and allows the testing of a variety of materials and utilizes a sealed fixture which contains the material to be tested or which has been exposed to the process to be tested by irradiating the windows of the heated fixture with the laser radiation of interest. The potential of the material to cause laser induced optical damages is determined.

SUMMARY OF THE INVENTION

A method and apparatus for testing materials for use in a laser resonator includes selecting a test fixture having a housing with an internal chamber volume selected to approximate the internal volume of a predetermined laser resonator and having a pair of sealed windows therein which are removably attached to the housing and having optical coatings selected to match the coating on the optics of a laser. The housing has a removable cover and a gas purging opening. A laser of a predetermined wavelength and power is mounted adjacent the test fixture and is aligned for directing the laser beam into one of the windows of the test fixture. A material is placed in the test fixture and a laser beam directed through the coated window into the fixed internal chamber for a predetermined period of time and thereafter the coated windows are examined for damage or contamination. The test fixtures are also cleaned and certified prior to testing so that a preselected test fixture can determine damage for selective materials used therein.

BRIEF DESCRIPTION OF THE DRAWINGS

Other objects, features, and advantages of the present invention will be apparent from the written description and the drawings in which.

DESCRIPTION OF THE PREFERRED EMBODIMENTS

Figure 1:
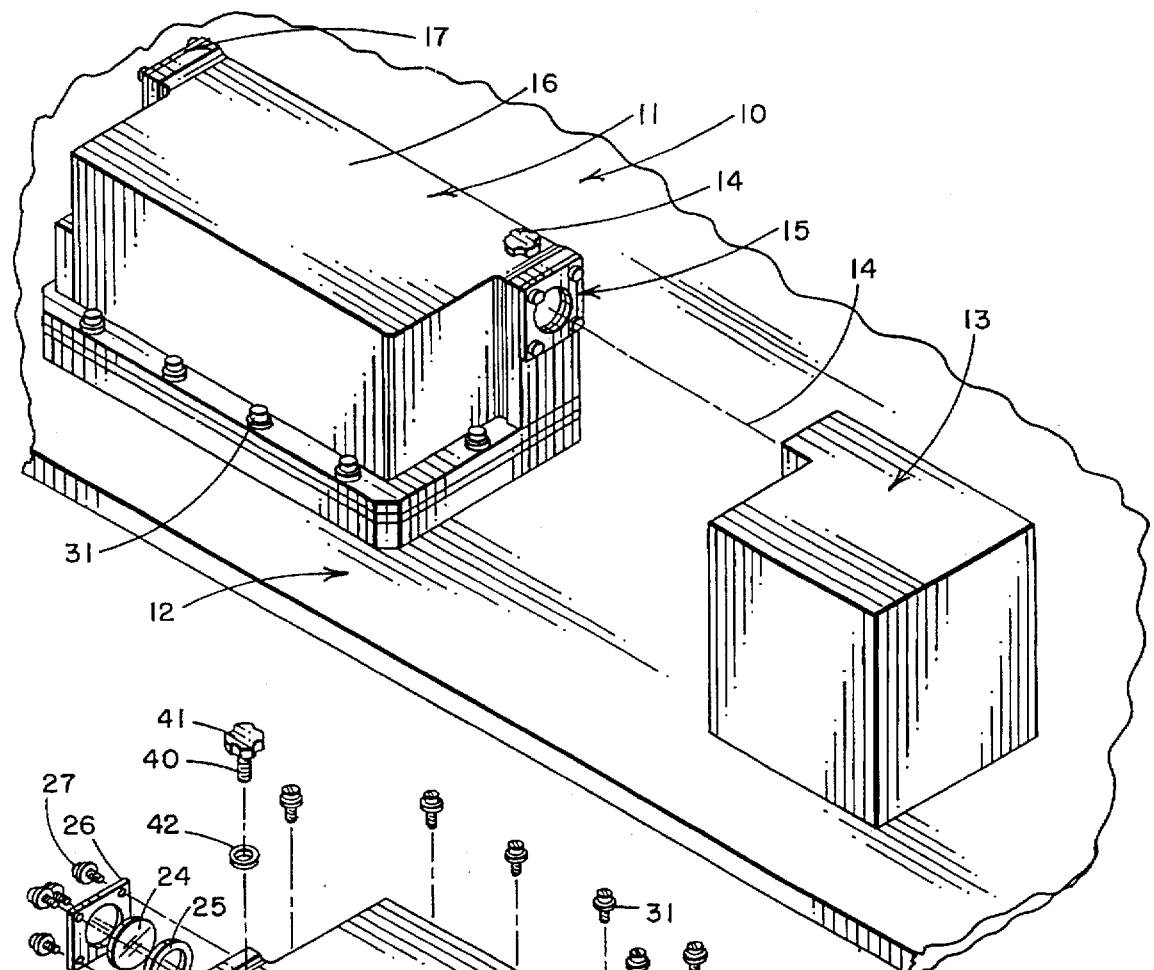
FIG. 1 is a perspective view of an apparatus for testing materials for use in a laser resonator in accordance with the present invention.
Figure 2:
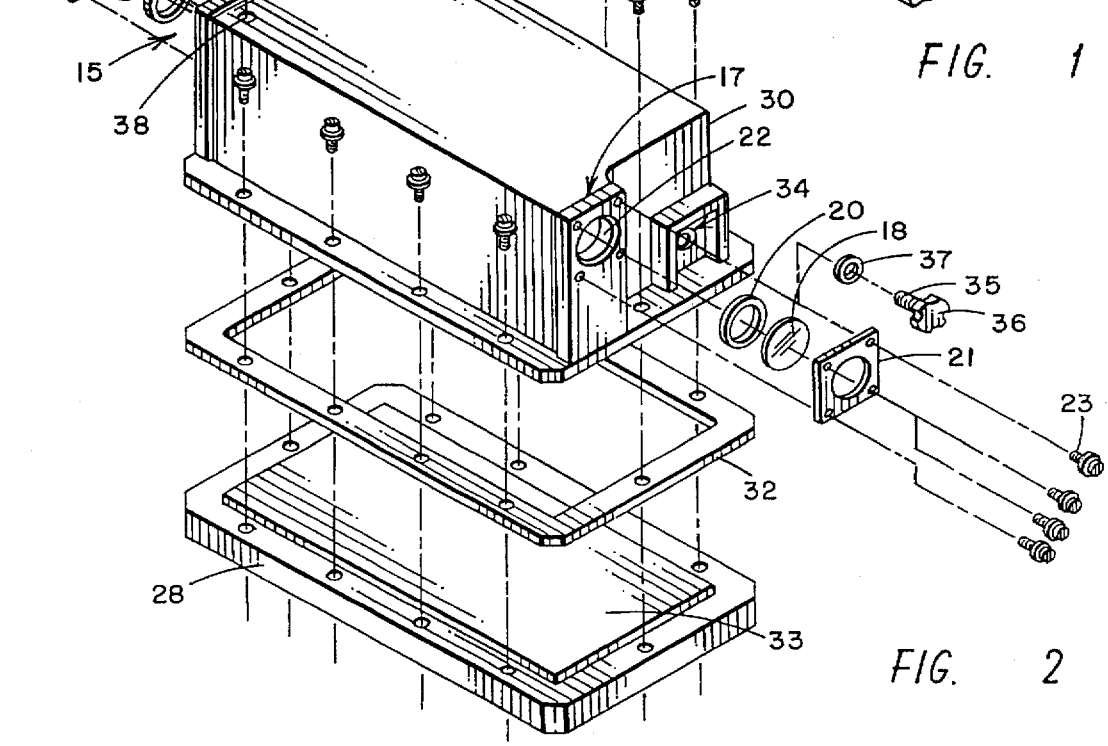
FIG. 2 is an exploded perspective view of the test fixture of FIG. 1.

Referring to the drawings FIGS. 1 and 2, a test set-up 10 having a test fixture 11 mounted to a fixture support 12 which has a laser 13 mounted to the base 12 with the output laser beam 14 directed towards a window 15 in the test fixture 11. The test fixture 11 is a sealed metal housing 16 having the window 15 at one end and a window 17 at the other end thereof. Windows 15 and 17 are aligned with the laser beam 14 being emitted from the laser 13. The window 15 includes a glass element 18 having predetermined coatings as desired and is attached to the housing 16 using an O-ring seal 20 and a bracket 21 for bolting the optics 18 over the opening 22 into the housing 16 with a plurality of bolts 23. A second window 17 has an optical glass opening 24 which may also have predetermined coatings. Window 17 has an O-ring seal 25 and is mounted to the housing 16 with a bracket 26 and a plurality of bolts 27. The test fixture 11 housing 16 has a base 28 and an upper housing 30 which is bolted to the base 28 with a plurality of bolts 31 and has a sealing gasket 32 therebetween. The base 28 provides a surface 33 for supporting materials thereon, if desired.

The windows 15 and 17 are removably mounted to the fixture 11 with O-ring seals so that they can be easily replaced when they become damaged. The chosen windows 18 and 24 materials and coatings is determined by the type of optical surface that is to be evaluated. The size of the box 16 is chosen such that it is similar in internal volume to a laser for which materials placed in the test fixture 11 are intended to be used so as to give a similar volume between the test fixture 11 and the laser being tested. The cover 30 mounts to the base plate 28 with a seal 32 which allows the easy introduction of materials to be tested. In addition, the test fixture 11 has a pair of sealable purge ports 34, one of which can be used for an inlet to inject gaseous materials to be tested while the other can be used to purge materials or, alternatively, to eject a purging gas into one of the inlets 34 and out the other. The ports 34 are each sealed with a sealing threaded bolt 35 having a handle 36 which is compressed onto an O-ring seal 37.

The basic test fixture 11 can have a housing 16 of aluminum or any material desired, which would be the same material used in the laser resonator cavity being tested for. The second purge opening 38 has a bolt 40 with a handle 41 and an O-ring seal 42 and is placed on top of the fixture housing 16. The test fixture as described in connection with FIGS. 1 and 2 is chosen to have an internal volume of the fixture 11 which simulates or is approximately the same size as the cavity of a laser resonator that is going to be utilized and the materials placed in the test fixture 11 are the same ones proposed to be used in the laser that the internal volume matches. The optics of the windows glass 15 and 22 is made with some of the same coatings as the optics for the laser to be used and the O-rings utilized with the seals are the same type to be used in the laser. The materials to be used in the housing are the type that are planned for the laser so that firing the laser beam 14 from the laser 13 through the glass openings and through the material for predetermined periods of time under predetermined temperatures will simulate the same kind of environment that the laser itself produces and will produce the same type of contamination or degradation of the materials and of the affect of the materials on the optics or optic coatings of the glass element 18 and 24 and on the seals as would be produced in the laser. The keys steps in the method to test for a potential of a material assembly or process to cause contamination induced optical damage in a laser resonator includes cleaning and assembling of the test fixture 11 and certification of the assembled test fixture as being cleaned and decontaminated, followed by the introduction of the materials into the test fixture 11 which has been assembled with the appropriate internal volume as well as the desired optical glass 18 and 24 coated with the desired coatings. Then mounting the test fixture to the base 12 and mounting the selected laser 13 with a predetermined power and wavelength output beam 14. The testing is done by having the laser 13 direct a beam through the windows 15 and 17 and through materials in the test fixture 11 housing 16 for a predetermined period of time. In addition, the temperature can be controlled for the test fixture 11 during the test. After the sample testing is complete, an inspection or final inspection of the fixture windows 18 and 24 takes place to see if there is any contamination or damage to the windows or the coatings for the windows and to any of the O-ring seals.

The cleaning step for the test fixture is performed to ensure that no residual contamination remains from previous tests. One means for cleaning the fixture involves the use of solvent soaks that will remove most types of contaminant residues. A particular implementation has been shown to work well on a silicone contaminant which utilizes solvent chemicals including uresolve in a first bath followed by a reagent alcohol in baths 2 and 3 along with a deionizing water in bath 4 followed by hexane/acetone 50/50 mixture in bath 5 along with acetone spectroscopic grade methanol and spectroscopic grade acetone.

Another fixture cleaning approach is to vacuum bake all of the test fixture parts at temperatures greater than 100° C. for several hours to remove all of the volatile residue contaminants. In cases where the fixture has been heavily contaminated, the combination of solvent cleaning plus vacuum baking has been found to be consistently effective. Certification of the test fixture verifies that no residual contaminants remain from previous tests. After the cleaning and assembly, the fixture can be placed in an oven and hot soaked for a minimum of 12 hours to ensure reduction of the residual contaminants. The soak temperature is chosen between 10 and 20° C. above the maximum operational temperature of the laser system for which the screening is being performed. The temperature of 80° C. has been used for tests.

After completion of the hot soak, the empty fixture is placed on a 95° C. hot plate and irradiated for a minimum of six hours with the laser of interest, operating at a power/energy level nominally representative of typical operating conditions. The fixture windows are then inspected with a high intensity lamp for any evidence of optical damage. If no optical damage is found, the fixture is considered certified and ready to use in a screening test.

For testing sample materials in assemblies, the cover is removed from the base plate, the material sample or assembly is placed on the base plate, and the cover is sealed back onto the base plate. For processes, the internal surfaces of the fixture, including the windows, are exposed to the process. For example, to test a purge process, the gas supply from the purge system to be tested is allowed to enter through one of the purge ports 34, 38 for several hours and the purge ports are then quickly sealed and the test initiated. Modification to the fixture can be made, as required, for testing for other processes. Once the sample has been introduced into the fixture, the fixture and sample are placed in an oven and hot soaked at the same temperature as the certification for a minimum of 12 hours. Sample testing is essentially a repeat of the certification process after the test sample has been introduced and consists of irradiation of the windows of the heated fixture with laser radiation at a power and wavelength which are characteristic of the laser resonator of interest using the same times and temperatures as are used in the certification. At the end of the irradiation process, the windows are again carefully inspected for optical damage with a high intensity lamp. If no damage or contamination is detected, the material assembly or processes which is tested is considered acceptable for use in the laser resonator of interest.

One example of material verification has been the testing in the present process of a blue flurosilicone material with a total mass loss (TML) of 0.32% and a collected volatile condensible material (CVCM) or CVCM material of 0.03% that was found to induce optical damage when tested as described above. When O-rings of this material were removed from a laser resonator built and then replaced by a material that passed the screening test, optical damage that had been occurring near the O-rings was eliminated. The invention allowed the screening of complete assemblies for their potential to cause laser induced optical damage.

Another example of prior practice screening processes showed that freon 113, a common industrial solvent, did not cause damage in concentration even as high as 13 parts per thousand (PPT) while toluene, another commonly used solvent, caused heavy damage at PPT levels when tested with a pulsed 1.06 μm laser radiation. This test showed that more emphasis should be placed on eliminating toluene contamination than on freon 113 contamination.

To practice the basic method of testing the material, the process for use in a laser resonator in accordance with the present invention includes the selecting of the sealable test fixture 11 for testing the materials and processes for use in a laser resonator which selected test fixture 11 has an internal volume selected to approximate the internal volume of a laser resonator that the materials or processes are to be used in. Test fixture has a pair of windows in the housing which are removably attached with O-ring seals. Coatings similar to the optical coatings in the actual resonator that the materials are to be used in should be on the windows so the housing has openings for the egress of purging materials. The process includes mounting the test fixture 11 onto a bed or base adjacent a laser 13 mounted on the same base having the laser output beam from the laser 13 directed towards one of the windows 15 or 17. The process includes placing materials to be tested in the selected test fixture either through the sealable cover or through the purge ports and directing a laser beam from the laser 13 through the coated window 15 and 17 and through the internal chamber of the housing 16 of the test fixture 11 and then examining the coated window for damage or contamination thereto.

The process can be expanded to cover the certification and testing through precleaning with either solvents or vacuum baking and the certification through hot soaks or raised temperatures and the testing of the materials placed in the test fixture, which have been heated or hot soaked and by heated a fixture and coated optics are examined for damage or contamination following the tests to determine what materials or processes can be used within the actual laser resonator.

It should be clear at this point that a method and an apparatus of testing materials and processes to determine materials for use in laser resonators has been provided which can provide more accurate results than prior material verification and process screenings. However, it should be clear that the present invention is not to be limited to the forms shown which are to be considered illustrative rather than restrictive.

We claim:

1. A method of testing materials for use in a laser resonator comprising the steps of:
   selecting a sealable test fixture for testing materials for use in a laser resonator, said fixture having a housing having an internal chamber volume selected to approximate the internal volume of a laser resonator, and said housing having a window therein removably attached thereto, said window having a coating selected to match the coating on the optics of a laser and said housing having a sealable cover covering an opening into said housing;
   mounting said selected test fixture adjacent a laser of predetermined wavelength and power and positioned for directing a laser beam through said window;
   placing a material to be tested into said selected test fixture through said sealable cover; and
   directing a laser beam from said laser through said window into said fixture internal chamber; and
   examining said window for damage thereto or contamination thereon; whereby a material for use in a predetermined laser can be tested for potential damage or contamination to a laser.

2. A method of testing materials for use in a laser resonator in accordance with claim 1 in which the step of selecting a sealable test fixture includes selecting a test fixture having a pair of windows aligned with each other.

3. A method of testing materials for use in a laser resonator in accordance with claim 1 including the step of cleaning said selected test fixture prior to filling with a material to be tested.

4. A method of testing materials for use in a laser resonator in accordance with claim 3 in which the step of cleaning said selected test fixture includes placing a partial vacuum thereon and baking said test fixture for a predetermined time and temperature.

5. A method of testing materials for use in a laser resonator in accordance with claim 3 in which the step of cleaning said selected test fixture includes cleaning with a series of selected solvents.

6. A method of testing materials for use in a laser resonator in accordance with claim 3 in which the step of cleaning said selected test fixture includes baking at a temperature above 100 C.

7. A method of testing materials for use in a laser resonator in accordance with claim 5 including the step of hot soaking said test fixture housing to at least 60 degrees C with a material to be tested therein.

8. A method of testing materials for use in a laser resonator in accordance with claim 5 including the step of hot soaking said test fixture housing to at least 80 degrees C with a material to be tested therein.

9. A method of testing materials for use in a laser resonator in accordance with claim 5 including the step of hot soaking said test fixture housing to at least 90 degrees C for at least six hours with a material to be tested therein.

10. A test fixture for testing materials for use in a laser resonator comprising:
    a test stand;
    a laser removable supported on said test stand;
    a test fixture having a housing having a chamber therein and a window removably mounted in said housing, said test fixture being removably attached to said test stand and having said window aligned with the output beam of said laser so that a laser beam can be directed into said chamber through said window and said housing having an opening therein and a sealable cover covering said opening; whereby materials being tested can be placed in said chamber and a laser beam of predetermined wavelength and power directed through said window into said chamber for testing for contamination or damage to said window from said materials.

11. A test fixture for testing materials for use in a laser resonator in accordance with claim 10 in which said test fixture housing has a pair of windows therein aligned with each other and with the output beam of said laser.

12. A test fixture for testing materials for use in a laser resonator in accordance with claim 11 in which said test fixture pair of windows each have a predetermined coating thereon and an O-ring seal mounted therearound to thereby seal each said window to said housing to thereby seal said chamber in said housing.

13. A test fixture for testing materials for use in a laser resonator in accordance with claim 11 in which said test fixture housing has a sealable purge port therein for purging gases from the chamber in said housing.

14. A test fixture for testing materials for use in a laser resonator in accordance with claim 13 in which said test fixture housing has a sealable inlet port therein for injecting gases into the chamber in said housing.

* * * * *